United States Patent
Yamazaki et al.

(10) Patent No.: US 6,184,402 B1
(45) Date of Patent: Feb. 6, 2001

(54) PROCESSES FOR THE PREPARATION OF METALLOCENE COMPLEXES

(75) Inventors: Hiroshi Yamazaki, Tokorozawa; Masato Nakano, Chiba; Seiki Mitani, Yokohama; Jun Saito, Kimitsu; Masato Harada, Yokohama; Mina Koyama, Tokyo, all of (JP)

(73) Assignee: Chisso Corporation, Tokyo (JP)

( * ) Notice: Under 35 U.S.C. 154(b), the term of this patent shall be extended for 0 days.

(21) Appl. No.: 09/509,645

(22) PCT Filed: Aug. 2, 1999

(86) PCT No.: PCT/JP99/04146

§ 371 Date: May 22, 2000

§ 102(e) Date: May 22, 2000

(87) PCT Pub. No.: WO00/08035

PCT Pub. Date: Feb. 17, 2000

(30) Foreign Application Priority Data

Aug. 3, 1998 (JP) .................................... 10-218730

(51) Int. Cl.[7] ................ C07F 17/00; C07F 7/00

(52) U.S. Cl. .................... 556/11; 556/12; 556/28; 556/53; 502/103; 502/117; 526/160; 526/943

(58) Field of Search ................... 556/11, 12, 28, 556/53; 502/103, 117; 526/160, 943

(56) References Cited

FOREIGN PATENT DOCUMENTS

| | | | |
|---|---|---|---|
| 9-47602 | * | 2/1997 | (JP) . |
| 10-109996 | * | 4/1998 | (JP) . |
| 10-259143 | * | 9/1998 | (JP) . |
| 11-122292 | * | 1/1999 | (JP) . |

OTHER PUBLICATIONS

Koyama et al., Chem. Lett., No. 11, pp. 1139–1140, 1998.*
Jany et al., Organometallics, vol. 16, No. 4, pp. 544–550, 1997.*

* cited by examiner

Primary Examiner—Porfirio Nazario-Gonzalez
(74) Attorney, Agent, or Firm—Leydig, Voit & Mayer, Ltd.

(57) ABSTRACT

Disclosed is a process for the preparation of metallocone complexes wherein stereoisomers of metallocene complexes formed at the time of synthesis can easily be separated. The gist of the present invention resides in separation of a part of an isomeric mixture of specific metallocene complexes bridged with a transition metal represented by the formula (1) as a complex having M—O bond. In particular, preferable is a process for separating a part of an isomeric mixture of a metallocene complex represented by the formula (2) as a $\mu$-oxo-complex represented by the formula (3).

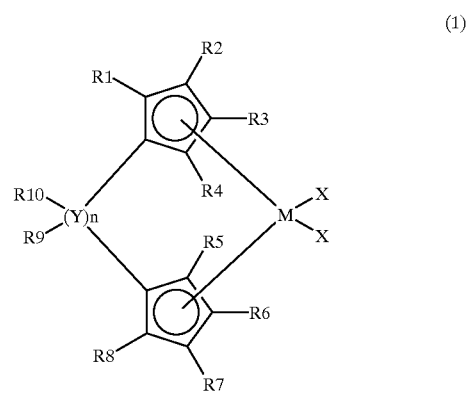

(1)

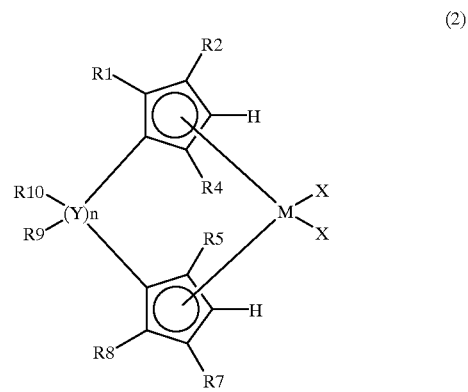

(2)

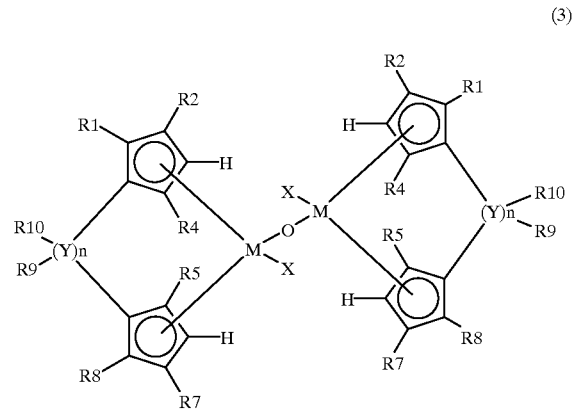

(3)

6 Claims, No Drawings

PROCESSES FOR THE PREPARATION OF METALLOCENE COMPLEXES

TECHNICAL FIELD

The present invention relates to a process for the preparation of metallocene complexes containing cyclopentadienyl rings as a ligand which are utilizable for the polymerization of olefins or the like.

BACKGROUND ART

It is known that in the polymerization of olefins, especially propylene, any of the a tactic polypropylene, isotactic polypropylene and syndiotactic polypropylene can be produced by choosing a ligand of a metallocene complex among uniform catalysts (a metallocene complex/aluminoxane) for polymerization of olefins (Makromol. Chem. Rapid. Commun. 1983, 4, 417–421; Angew. Chem., Int. Engl. 1985, 24, 507–508; J. Am. Chem. Soc. 1988, 110, 6255–6256; etc.)

Depending on the positions of substituents at the time of synthesis, metallocene complexes may permit the existence of stereoisomers. In the event a mixture of complex isomers formed on synthesis is straightforwardly used for polymerization of olefins where different olefin polymers are produced according to the different nature of the isomers, the resultant polymer will become a mixture of two different polymers. In case a uniform polymer is to be produced, therefore, the mixture of polymers has to be separated. Especially, a $C_2$ symmetrical crosslinking type metallocene complex tends to form a racemic form and a meso form of isomers in a ratio of 1:1 on its synthesis. On polymerization of propylene, the use of the racemic form permits the production of isotactic polypropylene while the use of the meso form permits the production of atactic polypropylene. Hence, the meso form has to be eliminated in case of producing isotactic polypropylene alone. Separation of the recemic form and the meso form is usually carried out by extraction with a solvent and recrystallization. For obtaining a highly pure racemic form, however, repeating of the separation operations was necessary so that efficiency of the production was extremely low.

In Japanese Laid-open Patent Appln. No.Hei. 10-67793, there is disclosed that a method of changing the racemic/meso ratio wherein unnecessary isomer is decomposed with a decomposing agent such as acidic hydrogen atom or a reactive halogen atom. This method pertains to changing of the racemic/meso ratio by decomposing either one of the isomers, and more precisely, the racemic form is decomposed with ethylene-bis(4,7-dimethylindenyl)zirconium dichloride to obtain the pure meso form.

A number of references are known concerning the reaction for converting a metallocene complex into a $\mu$-oxo-complex, for example, Inorganic Chemistry 15, No. 9, 1976 disclosing that dimethylhafnocene is brought into contact with water in the air to form $\mu$-oxo-bis(methylhafnocene) and Comprehensive Organometallic Chemistry 3, 1982, 572–576 disclosing that a metaflocene dihalide is converted into a $\mu$-oxo-complex in the presence of water and a base.

PROBLEMS TO BE SOLVED BY THE INVENTION

It is an object of the present invention to provide a process for preparing metallocene complexes wherein stereoisomers of metallocene complexes formed on synthesis can easily be resolved into their isomers.

DISCLOSURE OF THE INVENTION

As a result of extensive research made to achieve the aforesaid object, it has now been found by the inventors that a reaction for replacing a substituent on the central metal of a metallocene complex by M—O bond differs in reactivity according to the isomer, and a part or all of a specific isomer can be converted into a complex having M—O bond and that the complex having M—O bond is significantly different in solubility from the original metallocene complex so that the complex having M—O bond can easily be separated according to an ordinary separation method, e.g. extraction or recrystallization while purity of unreacted isomer can efficiently be increased. The present invention has been accomplished on the basis of the above finding.

Especially for an isomeric mixture of the racemic form and the meso form of a bridged metllocene complex, a reaction for forming a $\mu$-oxo-complex is carried out whereby the meso form is preferentially converted into the $\mu$-oxo-complex. Thus, the purity of the racemic form can easily be increased by separating the $\mu$-oxo-complex thereform. If the total amount of the meso form is converted into the $\mu$-oxo-complex, the racemic form will be obtained in a higher purity.

In accordance with the present invention, there is provided a process for the preparation of metallocene complexes which comprises converting a part of an isomeric mixture of a metallocene complex represented by the formula (1):

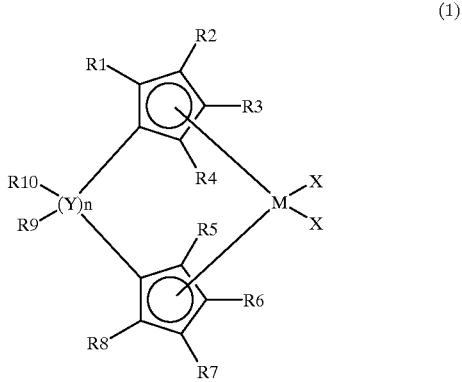

wherein M stands for a transition metal belonging Group III, IV, V, VI Lantanoid or Actinoid of the Periodic Table, n stands for an integer of 1 or 2, Y stands for carbon, silicon, germanium or tin, X's may be the same or different and each independently stands for a halogen atom, a halogenoid atomic group, a hydrocarbon group having 1–20 carbon atoms which may contain a silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in the 5-membered or 6-membered ring or rings thereof and which may be substituted on the ring or rings thereof by other substituents, R1, R2, R3, R4, R5, R6, R7, R8, R9 and R10 may be the same or different and each stands for hydrogen, an alkyl group having 1–20 carbon atoms, a cycloalkyl group having 3–20 carbon atoms, an alkenyl group with 2–20 carbon atoms, an aryl group having 6–20 carbon atoms, an alkylaryl group having 7–20 carbon atoms, or an aralkyl group having 7–20 carbon atoms with the proviso that these groups may contain a silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in the 5-membered or 6-membered ring or rings thereof and which may be substiututed on the ring or rings by other substituents with the proviso that the adjacent substituents on the cyclopentadienyl groups may form together a cyclic structure having 5–8 carbon atoms and the cyclic structure may be an aromatic ring, and that R9 and R10 may form together with Y a cyclic structure having 4–8 atoms and which may contain oxygen, sulfur and nitrogen, into a complex containing M—O bond, and then separating it.

According to the present invention, there is also provided a process for the preparation of metallocene complexes which comprises converting a part of an isomeric mixture of a metallocene complex represented by the formula (2):

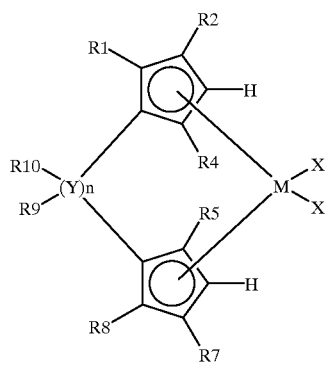

(2)

wherein M stands for titanium, zirconium or hafnium, n stands for an integer of 1 or 2, Y stands for carbon, silicon or germanium, X's may be the same or different and each independently stands for a halogen atom, a halogenoid atomic group, a hydrocarbon group having 1–20 carbon atoms which may contain a silicon, germanium, oxygen, sulfur, or nitrogen, R2 and R7 may be the same or different and each stands for an alkyl group having 1–20 carbon atoms, a cycloalkyl group having 3–20 carbon atoms, an alkenyl group having 2–20 carbon atoms, an aryl group having 6–20 carbon atoms, an alkylaryl group having 7–20 carbon atoms, or an aralkyl group having 7–20 carbon atoms which may include silicon, germanium, oxygen, sulfur and nitrogen, R1, R4, R5, and R8 may be the same or different and each stands for hydrogen, an alkyl group having 1–20 carbon atoms, a cycloalkyl group having 3–20 carbon atoms, an alkenyl group having 2–20 carbon atoms, an aryl group having 6–20 carbon atoms, an alkylaryl group having 7–20 carbon atoms, an aralkyl group having 7–20 carbon atoms which may include silicon, germanium, oxygen, sulfur, and nitrogen, or a monocyclic or polycyclic heteroaromatic group which may contain a hetero atom or atoms selected from the group consisting of oxygen atoms, sulfur atoms and nitrogen atoms in the 5-membered or 6-membered ring or rings thereof and which may be substituted on the ring or rings by other substituents with the proviso that R1 and R2 as well as R7 and R8 may form together a cyclic structure having 5–8 carbon atoms which may be an aromatic ring, and that R7 and R8 may form together a cyclic structure having 4–8 carbon atoms which may include oxygen, sulfur and nitrogen, into a μ-oxo-complex represented by the formula (3).

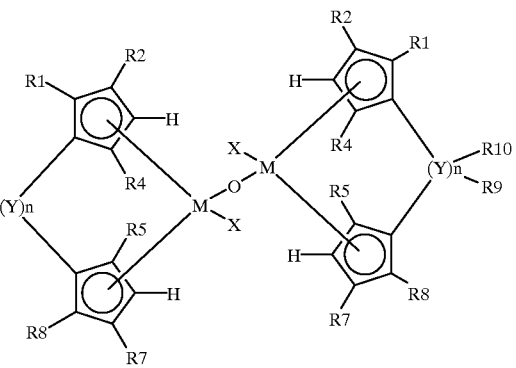

(3)

and then separating the μ-oxo-complex.

According to the present invention, there is further provided a process for the preparation of metallocene complexes which comprises converting a part or the total amount of a meso form out of a mixture of the meso form and a racemic form of a metallocene complex represented by the aforesaid formula (2) into a μ-oxo-complex represented by the aforesaid formula (3) and then separating the μ-oxo-complex.

According to the present invention, there is still further provided a process for the preparation of metallocene complexes which comprises reacting a mixture of a a meso form and a racemic form of a metallocene complex represented by the aforesaid formula (2) wherein X stands for a halogen atom with water in the presence of a base thereby converting a part or the total amount of the meso form into a μ-oxo-complex represented by the aforesaid formula (3) and then separating the μ-oxo-complex.

A BEST EMBODIMENT FOR CARRYING OUT THE INVENTION

A maximum characteristic feature of the process for the preparation of metallocene complexes of the present invention resides in converting a part of an isomeric mixture of a metallocene complex represented by the formula (1) into a complex having M—O bond and separating it.

It is especially preferable that among metallocene complexes included in the formula (1), a mixture of isomeric mixture of metallocene complexes shown in the formula (2) is converted partially into a μ-oxo-complex represented by the formula (3) and the μ-oxo-complex is then separated.

Below is a detailed description on the construction and effect of the present invention.

Metallocene complexes utilizable in the present invention are those represented by the aforesaid formula (1).

In this formula, M stands for a transition metal belonging to Group III, IV, V, VI and Lantanoid and Actinoid of the Periodic Table, preferably titanium, zirconium, or hafnium belonging to Group IV. n is an integer of 1 or 2 and Y stands for carbon, silicon, germanium, and tin. preferably carbon silicon and germanium.

The substituents X's on the zirconium may be the same or different and each stands for a halogen atom, a halogenoid atomic group or a hydrocarbon group having 1–20 carbon atoms. Examples of the halogen include fluorine, chlorine, bromine and iodine. Preferable is chlorine, bromine and iodine. Examples of the halogenoid atomic group include the grouping of NCS, NCO, $N_3$, $N(CN)_2$, $C(CN)_3$, $C(CN)_2$, and (NO). Examples of the hydrocarbon group having 1–20 carbon atoms include an alkyl group, a cycloalkyl group, an aryl group, an alkylaryl and an aralkyl group.

The substituents R1, R2, R3, R4, R5, R6, R7, R8, R9, and R10 may be the same or different and each independently stands for hydrogen, an alkyl group having having 1–20 carbon atoms, a cycloalkyl group having 3–20 carbon atoms, an alkenyl group having a 2–20 carbon atoms, an aryl group having 6–20 carbon atoms, an alkylaryl group having 7–20 carbon atoms, an aralkyl group having 7–20 carbon atoms which may contain oxygen, sulfur and nitrogen, or a monocyclic or polycyclic heteroaryl group which may contain a hetero atom or atoms selected from the group consisting of oxygen atoms, sulfur atoms and nitrogen atoms in the 5-membered or 6-membered ring or rings thereof and which may be substituted on the ring or rings thereof by other substituents. Illustrative of these groups are for example, methyl group, ethyl group, isopropyl group, tert-butyl group, cyclopentyl group, cyclohexyl group, vinyl group, allyl group, phenyl group, naphthyl group, tolyl group, dimethylphenyl group, benzyl group, phenylethyl group, trimethylsilyl group, trimethylgermyl group, furyl group, thienyl group, pyridyl group.

Any adjacent substituents on the cyclopentadienyl ring or rings may form a cyclic structure having 5–8 carbon atoms and the cyclic structure may be an aromatic ring. In case R1 and R2 are fused together to form an aromatic group as a cyclic structure having 6 carbon atoms, for example, it will become an indenyl ligand. The cyclic structure may have a substituent or substituents.

In the event a metallocene complex is converted into a $\mu$-oxo-complex, the starting complex wherein R3 and R6 are hydrogen and R2 and R7 are substituents other than hydrogen is easily convertible into the $\mu$-oxo-complex and so is preferable as it is higher in selectivity of isomers.

The substituents R9 and R10 in a bridging portion may form a cyclic structure having 4–8 carbon atoms wherein silicon, germanium, oxygen, sulfur and nitrogen may be contained.

An isomeric mixture of a metallocene complex of the formula (1) can be prepared, for example, according to the following process: A substituted cycloalkadiene having substituents R1–R4 is anionized by the reaction with a metal salt type base to form a substituted cycloalkadiene anion which is then reacted at a molar ratio of 1:1 with a substituted cycloalkadiene compound connected through $(Y)_n$ to $(Y)_n$—$(X^1)_2$ wherein $X^1$ stands for a hydrogen atom or a halogen atom, to form a compound wherein two cycloalkadienes are connected each other through Y. The latter compound is then reacted with a metal salt type base to form a dianion wherein each of the cycloalkadiene ring is anionized. The dianion is then reacted with a transition metal compound $(X)_2$—M—$(X^2)_2$ wherein $X^2$ stands for a hydrogen atom or a halogen atom to obtain the isomeric mixture of a metallocne complex.

Examples of the complex having M—O bond include a compound wherein one of X's on M is substituted to form M—O—R (wherein R stands for hydrogen, an alkyl group having 1–20 carbon atoms, a cycloalkyl group having 3–20 carbon atoms, an alkenyl group having 2–20 carbon atoms, an aryl group having 6–20 carbon atoms. an alkylaryl group having 7–20 carbon atoms, an aralkyl group having 7–20 carbon atoms, with the proviso that these groups may contain silicon, germanium, oxygen, sulfur and nitrogen, or a monocyclic or polycyclic heteroaromatic group which may contain a hetero atom or atoms selected from the group consisting of oxygen atoms, sulfur atoms and nitrogen atoms in the 5-membered or 6-membered ring or rings thereof and which may be substituted on the ring or rings thereof by other substituents, for example, methyl group, ethyl group, isopropyl group, tertbutyl group, cyclopentyl group, cyclohexyl group, vinyl group, allyl group, phenyl group, naphthyl group, tolyl group, dimethylphenyl group, benzyl group, phenylethyl group, trimethylsilyl group, trimethylgermyl group, furyl group, thienyl group, pyridyl group), a compound wherein a central metal M is carried on a support such as silica gel through oxygen, and a $\mu$-oxo-complex wherein the central metals of two molecules of a metallocene complex is crosslinked via oxygen.

As a means for converting a part of isomeric mixture of a metallocene complex shown by the formula (1), there can be mentioned a process wherein the isomeric mixture is reacted with ROH, ROLi, or RONa, a process wherein the isomeric mixture is reacted with a silica gel the surface of which has been modified with —OLi or —ONa, and a process wherein the isomeric mixture is reacted with water to form a $\mu$-oxo-complex.

Especially preferable is a process wherein the reaction is intended to form a $\mu$-oxo-complex, since it is higher in selectivity of the isomer and is easy for separation.

Selectivity of isomers depends chiefly on the reactivity of X so that an isomer having X of less steric hindrance is preferentially reacted to form a complex having M—O bond. This fact will be explained, for example, in connection with the reaction for a mixture of a racemic form and a meso form of dimethylsilylene-bis(2,3,5-trimethylcyclopentadienyl)zirconium dichloride to prepare a $\mu$-oxo-complex. In case of the racemic form, both chlorines are equivalent and only one 3-methyl group is present in the vicinity of each chorine. In the case of the meso form, on the other hand, two methyl groups are present in either of chlorine atoms but the other chlorine is less steric hindrance of 3-methyl group. Accordingly, when water is reacted with the mixture, water is preferentially reacted with chlorine of less steric hindrance in the meso form to afford a $\mu$-oxo-complex.

The reaction for forming a $\mu$-oxo-complex chiefly due to the reaction of water with a metallocene compound is well known and a $\mu$-oxo-complex is easily obtained. In case of a metallocene dihalide wherein a halogen is a substituent on the central metal, it is necessary in majority of the cases to react the metallocene complex with water in the presence of a base.

No limitation exists in the amount of water to be reacted with an isomeric mixture but it is preferable that 0.01–10 equiamount of water is preferable for an isomeric mixture to be converted into the $\mu$-oxo-complex. In case either one of the isomers is to be eliminated entirely, however, at least 0.5 equimolar water will be necessary for an isomeric mixture to be converted into a $\mu$-oxo-complex. Further, it is necessary to consider the amount of water or moisture existent in the air, reagents and solvents. In case the reaction is carried out with a small amount of a metallocene complex, the reaction proceeds with water present in the air, reagents or solvents so that it is sometimes unnecessary to add water.

A temperature for the reaction is such that the metallocene complex used is not decomposed. Thus, the temperature is preferably within the range of –80° C. to 80° C.

No limitation exists in the reaction solvent so far as the metallocene complex used is not decomposed. Examples of the solvent include chloroform, dichloromethane, hexane, toluene, diethyl ether, tetrahydrofuran (THF), etc.

In the event a metallocen complex is not reacted with water alone, the presence of a base becomes necessary. Mentioned as a utilizable base are inorganic basic compounds such as lithium hydroxide, sodium hydroxide, and potassium hydroxide and amines represented by the formula (4):

$$R_pNH_{3-p} \qquad (4)$$

wherein p stands for an integer of 0–3, R is an alkyl group having 1–20 carbon atoms, a cycloalkyl group having 3–20 carbon atoms, an alkenyl group with 2–20 carbon atoms, an aryl group having 6–20 carbon atoms, an alkylaryl group having 7–20 carbon atoms, or an aralkyl group having 7–20 carbon atoms, when p stands for 2 or 3, R's may be the same or different and may be combined together to form a cyclic structure having 5–8 carbon atoms which may contain silicon, oxygen, sulfur and nitrogen.

Illustrative of the amine are, for example, ammonia, ethylamine, diethylamine, triethylamine, aniline, pyrrolidine, pyridine, and tetramethylethylene diamine.

In case a strongly basic substance is used, there is a possibility of decomposition in a metallocene complex used. Accordingly, the use of a weak base such as an amine is preferable. No special limitation exists in the amount of the basic substance used but 0.01–10 equiamount, preferably 0.8–1.2 equiamount of the basic substance is used for a metallocene complex to be converted into a $\mu$-oxo-complex.

After converting a part of the isomeric mixture of a metallocene complex into a complex having M—O bond, unreacted isomer is obtained by removing the complex having M—O bond. An ordinary separation method, such as extraction with a solvent or recrystallization can be used for this separation. As extraction with a solvent, the reaction liquid is dried until dryness and the residue is extracted with a solvent and the solution is stirred and filtered, or a continuous extraction using a Soxlet extractor may be mentioned. Mentioned as the recrystallization method, the reaction mixture is dissolved with a solvent and the solution is cooled or mixed with a poor solvent to precipitate crystals which are then separated.

Illustrative of the solvent are, for example, pentane, hexane, toluene. dichoromethane, THF, diethyl ether, diisopropyl ether, and a mixture of these solvents.

As a $\mu$-oxo-complex is especially inferior in solubility to the starting metallocene complex, the former can easily be removed by extraction with a solvent.

As a general property of a $\mu$-oxo-complex, it undergoes reaction with a proton reagent to split off the —O-bridge. In case X in the resultant $\mu$-oxo-complex is a halogen, therefore, the separated $\mu$-oxo-complex is reacted with HX to split off the —O-bridge thereby regenerating the original metallocene complex. It follows that an isomeric form of a metallocene which was once converted into the $\mu$-oxo-complex from the isomeric mixture can also be obtained in a high purity.

Illustrative of the metallocene complex involved in the formula (1) are, for example, dimethylsilylene-bis(3-methylcyclopentadienyl)zirconium dichloride, dimethylsilylene-bis(2,4-dimethylcyclopentadienyl)zirconium dichloride, dimethyl-silylene-bis(2,3,5-trimiethylcyclopentadienyl)zirconium dichloride; dimethylsilylene-bis(3-tert-butylcyclopentadienyl)zirconium dichoride, dimethylsilylene-bis(4-tert-butyl-2-methylcyclopentadienyl)zirconium dichloride, dimethylsilylene-bis(3-tert-butyl-2,5-dimethylcyclopentadienyl)zirconium dichloride; dimethylsilylene-bis(3-phenylcyclopentadienyl)zirconium dichloride, dimethylsilylene-bis(4-phenyl-2-methylcyclopentadienyl)zirconium dichloride, dimethylsilylene-bis(3-phenyl-2,5-dimethylcyclopentadienyl)zirconium dichloride; dimethylgermylene-bis(3-methylcyclopentadienyl)zirconium dichloride, dimethylgermylene-bis(2,4-dimethylcyclopentadienyl)zirconium dichloride, dimethylgermylene-bis(2,3,5-trimethylcyclopentadienyl)zirconium dichloride; dimethylgermylene-bis(3-tert-butylcyclopentadienyl)zirconium dichloride, dimethylgermylene-bis(4-tert-butyl-2-methylcyclopentadienyl)zirconium dichloride, dimethylgermylene-bis(3-tert-butyl-2,5-dimethylcyclopentadienyl)zirconium dichloride, dimethylgermylene-bis(3-phenylcyclopentadienyl)zirconium dichloride, dimethylgermylene-bis(4-phenyl-2-methylcyclopentadienyl)zirconium dichloride, dimethylgermylene-bis(3-phenyl-2,5-dimethylcyclopentadienyl)zirconium dichloride, dimethylsilylene-bis(3-methylcyclopentadienyl)hafnium dichloride, dimethylsilylene-bis(2,4-dimethylcyclopentadienyl)hafnium dichloride, dimethylsilylene-bis(2,3,5-tri-methylcyclopentadienyl)hafnium dichloride; dimethylsilylene-bis(3-tert-butylcyclopentadienyl)hafnium dichloride, dimethylsilylene-bis(4-tert-butyl-2-methylcyclopentadienyl)hafnium dichloride, dimethylsilylene-bis(3-tert-butyl-2,5-dimethylcyclopentadienyl)hafnium dichloride; dimethylsilylene-bis(3-phenylcyclopentadienyl)hafnium dichloride, dimethylsilylene-bis(4-phenyl-2-methylcyclopentadienyl)hafnium dichloride, dimethylsilylene-bis(3-phenyl-2,5-dimethylcyclopentadienyl)hafnium dichloride; dimethylgermylene-bis(3-methylcyclopentadienyl)hafnium dichloride, dimethylgermylene-bis(2,4-dimethylcyclopentadienyl)hafnium dichloride, dimethylgermylene-bis(2,3,5-trimethylcyclopentadienyl)hafnium dichloride; dimethylgermylene-bis(3-tert-butylcyclopentadienyl)hafnium dichloride, dimethylgermylene-bis(4-tert-butyl-2-methylcyclopentadienyl)hafnium dichloride, dimethylgermylene-bis(3-tert-butyl-2,5-dimethylcyclopentadienyl)hafnium dichloride; dimethylgermylene-bis(3-phenylcyclopentadienyl)hafnium dichloride, dimethylgermylene-bis(4-phenyl-2-methylcyclopentadienyl)hafnium dichloride, dimethylgermylene-bis(3-phenyl-2,5-dimethylcyclopentadienyl)hafnium dichloride; silacyclopentane-bis(3- methylcyclopentadienyl)zirconium dichloride, silacyclopentane-bis(2,4-dimethylcyclopentadienyl)zirconium dichloride, silacyclopentane-bis(2,3,5-trimethylcyclopentadienyl)zirconium dichloride, silacyclopentane-bis(3-tert-butylcyclopentadienyl)zirconium dichloride; silacyclopentane-bis(4-tert-butyl-2-methylcyclopentadienyl)zirconium dichloride, silacyclopentane-bis(3-tert-butyl-2,5-dimethylcyclopentadienyl)zirconium dichloride, silacyclopentane-bis(3-phenylcyclopentadienyl)zirconium dichloride, silacyclopentane-bis(4-phenyl-2-methylcyclopentadienyl)zirconium dichloride, silacyclopentane-bis(3-phenyl-2,5-dimethylcyclopentadienyl)zirconium dichloride; silacyclobutane-bis(3-methylcyclopentadienyl)-zirconium dichloride, silacyclobutane-bis(2,4-dimethylcyclopentadienyl)zirconium dichloride, silacyclobutane-bis(2,3,5-trimnethylcyclopentadienyl) zirconium dichloride; silacyclobutane-bis(3-tert-butylcyclopentadienyl)zirconium dichloride, silacyclobutane-bis(4-tert-butyl-2-methylcyclopentadienyl) zirconium dichloride, silacyclobutane-bis(3-tert-butyl-2,5-dimethylcyclopentadienyl)zirconium dichloride; silacyclobutane-bis(3-phenylcyclopentadienyl)zirconium dichloride, silacyclobutane-bis(4-phenyl-2-methylcyclopentadienyl)zirconium dichloride, silacyclobutane-bis(3-phenyl-2,5-dimethylcyclopentadienyl)zirconium dichloride; dimethylsilylene-bis(tetrahydroindenyl)zirconium dichloride, dimethylsilylene-bis(2-methyltetrahydroindenyl)zirconium dichloride, dimethylsilylene-bis(indenyl)zirconium dichloride, dimethylsilylene-bis(2-methylindenyl)zirconium dichloride, dimethylsilylene-bis(2-methyl-4,5-benzoindenyl)zirconium dichloride, dimethylsilylene-bis(2-methyl-4-phenylindenyl) zirconium dichloride, dimethylsilylene-bis(2-methyl-4-naphthylindenyl)zirconium dichloride, dimethylsilylene-bis(1-cyclopentaphenanthryl)zirconium dichloride, dimethylsilylene-bis[1-(2-methylcyclopenta)phenanthryl] zirconium dichloride, dimethylsilylene-bis[1-(2-methylcyclopenta)phenanthryl]zirconium dichloride; dimethylgermylene-bis(tetrahydroindenyl)zirconium dichloride, dimethylgermylene-bis(2-methyltetrahydroindenyl)zirconium dichloride, dimethylgermylene-bis(indenyl)zirconium dichloride, dimethylgermylene-bis(2-methylinenyl)zirconium dichloride, dimethylgermylene-bis(2-methyl-4,5-benzoindenyl)zirconium dichloride, dimethylgermylene-bis(2-methyl-4-phenylindenyl)zirconium dichloride , dimethylgermylene-bis(2-methyl-4-naphthylindenyl) zirconium dichloride, dimethylgermylene-bis(1-cyclopentaphenanthryl)zirconium dichloride, dimethylgermylene-bis[1-(2-methylcyclopenta)phenanthryl]zirconium dichloride; dimethylsilylene(3-methylcyclopentadienyl)(2,3,5-trimethylcyclopentadienyl) zirconium dichloride, dimethylsilylene(2,4-dimethylcyclopentadieny)(2,3,5-trimethylcyclopentadienyl) zirconium dichloride; dimethylsilylene(3-tert-butylcyclopentadienyl)(2,3,5-trimethylcyclopentadienyl) zirconium dichloride, dimethylsilylene(2-methyl-4-tert-butylcyclopentadieny)(2,3,5-trimethylcyclopentadienyl) zirconium dichloride, dimethylsilylene(2,5-dimethyl-3-tert-butylcyclopentadieny)(2,3,5-trimethylcyclopentadienyl) zirconium dichloride; dimethylsilylene(3-phenylcyclopentadienyl)(2,3,5-trimethylcyclopentadienyl) zirconium dichloride, dimethylsilylene(2-methyl-4-phenylcyclopentadieny)(2,3,5-trimethylcyclopentadienyl)- zirconium dichloride, dimethylsilylene(2,5-dimethyl-3-phenylcyclopentadieny)(2,3,5-trimethylcyclopentadienyl) zirconium dichloride; dimethylgermylene(3-methylcyclopentadienyl)(2,3,5-trimethylcyclopentadienyl) zirconium dichloride, dimethylgermylene(2,4-dimethylcyclopentadienyl)(2,3,5-trimethylcyclopentadienyl) zirconium dichloride; dimethylgermylene(3-tert-butylcyclopentadienyl)(2,3,5-trimethylcyclopentadienyl)-zirconium dichloride, dimethylgermylene(2-methyl-4-tert-butylcyclopentadienyl)(2,3,5-trimethylcyclopentadienyl)zirconium dichloride, dimethylgermylene(2,5-dimethyl-3-tert-butylcyclopentadienyl)(2,3,5-trimethylcyclopentadienyl) zirconium dichloride; dimethylgermylene(3-phenylcyclopentadienyl)(2,3,5-trimethylcyclopentadienyl) zirconium dichloride, dimethylgermylene(2-methyl-4-phenylcyclopentadienyl)(2,3,5-trimethylcyclopentadienyl) zirconium dichloride, dimethylgermylene(2,5dimethyl-3-phenylcyclopentadienyl)(2,3,5-trimethylcyclopentadienyl) zirconium dichloride; dimethylsilylene(3-methylcyclopentadienyl)(2-methylindenyl)zirconium dichloride, dimethylsilylene(2,3,5-trimethylcyclopentadienyl)(2-methylindenyl)zirconium dichloride, dimethylsilylene(3-tert-butylcyclopentadienyl)(2-methylindenyl)zirconium dichloride, dimethylsilylene(3-phenylcyclopentadienyl)(2-methylindenyl)zirconium dichloride, dimethylsilylene(3-phenyl-2,5-dimethylcyclopentadienyl)(2-methylindenyl)zirconium dichloride; dimethylsilylene(3-methylcyclopentadienyl)(2,3-dimethylindenyl)zirconium dichloride, dimethylsilylene(2,4-dimethylcyclopentadienyl)(2,3-dimethylindenyl) zirconium dichloride, dimethylsilylene(3-tert-butylcyclopentadienyl)(2,3-dimethylmethylindenyl) zirconium dichloride, dimethylsilylene(3-phenylcyclopentadienyl)(2,3-dimehlethylindenyl)zirconium dichloride, dimethylsilylene(3-phenyl-2,5-dimethylcyclopentadienyl)(2,3-dimethylindenyl)zirconium dichloride; dimethylgermylene(3-methylcyclopentadienyl)(2-methylindenyl)zirconium dichloride, dimethylgermylene(2,4-dimethylcyclopentadienyl)(2-methylindenyl)zirconium dichloride, dimethylgermylene(2,3,5-trimethylcyclopentadienyl)(2-methylindenyl)zirconium dichloride, dimethylgermylene(3-tert-butylcyclopentadienyl)(2-methylindenyl)zirconium dichloride, dimethylgermylene(3-phenylcyclopentadienyl)(2-methylindenyl)zirconium dichloride, dimethylgermylene(3-phenyl-2,5-dimethylcyclopentadienyl)(2-methylindenyl) zirconium dichloride; dimethylgermylene(3-methylcyclopentadienyl)(2,3-dimethylindenyl)zirconium dichloride, dimethylgermylene(2,4-dimethylcyclopentadienyl)(2,3-dimethylindenyl) zirconium dichloride, dimethylgermylene(2,3,5-trimethylcyclopentadienyl)(2,3-dimethylindenyl)zirconium dichloride, dimethylgermylene(3-tert-butylcyclopentadienyl)(2,3-dimethylindenyl)zirconium dichloride, dimethylgermylene(3-phenylcyclopentadienyl) (2,3-dimethylindenyl)zirconium dichloride, dimethylgermylene(3-phenyl-2,5-dimethylcyclopentadienyl)(2,3-dimethylindenyl)zirconium dichloride; ethylene-bis(3-methylcyclopentadienyl) zirconium dichloride, ethylene-bis(2,4-dimethylcyclopentadienyl)zirconium dichloride, ethylene-bis(2,3,5-trimethylcyclopentadienyl)zirconium dichloride, ethylene-bis(4-tert-butyl-2-methylcyclopentadienyl) zirconium dichloride, ethylene-bis(3-tert-butyl-2,5-dimethylcyclopentadienyl)zirconium dichloride, ethylene-bis(3-phenylcyclopentadienyl)zirconium dichloride, ethylene-bis(4-phenyl-2-methylcyclopentadienyl)zirconium dichloride, ethylene-bis(3-phenyl-2,5-dimethylcyclopentadienyl)zirconium dichloride, ethylene-bis(tetra-hydroindenyl)zirconium dichloride; ethylene-bis (2-methylindenyl)zirconium dichloride, ethylene-bis(2-methyl-4,5-benzoindenyl)zirconium dichloride, ethylene-bis(2-methyl-4-phenylindenyl)zirconium dichloride, ethylenebis(2-methyl-4-naphthylindenyl)zirconium dichloride, ethylene-bis(1-cyclopentaphenanthryl) zirconium dichloride, ethylene-bis[1-(2-methylcyclopenta) phenanthryl]zirconium dichloride; ethylene-bis(3-methylcyclopentadienyl)hafnium dichloride, ethylene-bis(2,4-dimethylcyclopentadienyl)hafnium dichloride, ethylene-bis(2,3,5-trimethylcyclopentadienyl)hafnium dichloride; ethylene-bis(3-tert-butylcyclopentadienyl)hafnium dichloride, ethylene-bis(4-tert-butyl-2-methylcyclopentadienyl)hafnium dichloride, ethylene-bis (3-tert-butyl-2,5-dimethylcyclopentadienyl)hafnium dichloride; ethylene-bis(3-phenylcyclopentadienyl)hafnium dichloride, ethylene-bis(4-phenyl-2-methylcyclopentadienyl)hafnium dichloride; ethylene-bis(3-phenyl-2,5-dimethylcyclopentadienyl)hafnium dichloride; ethylene-bis(tetrahydroindenyl)hafnium dichloride, ethylene-bis(indenyl)hafnium dichloride, ethylene-bis(2-methylindenyl)hafnium dichloride, ethylene-bis(2-methyl-4,5-benzoindenyl)hafnium dichloride, ethylene-bis(2-methyl-4-phenylindenyl)hafnium dichloride, ethylene-bis(2-methyl-4-naphthylindenyl)hafnium dichloride, ethylene-bis(1-cyclopentaphenanthryl)hafnium dichloride, ethylene-bis[1-(2-methylcyclopenta)phenanthryl]hafnium dichloride; dimethylsilylene-bis(3-tolylcyclopentadienyl)zirconium dichloride, dimethylsilylene-bis(4-tolyl-2-methylcyclopentadienyl)zirconium dichloride, dimethylsilylene-bis(3-tolyl-2,5-dimethylcyclopentadienyl)zirconium dichloride; dimethylsilylene-bis(3-ethylphenylcyclopentadienyl)zirconium dichoride, dimethylsilylene-bis(4-ethylphenyl-2-methylcyclopentadienyl)zirconium dichloride, dimethylsilylene-bis(3-ethylphenyl-2,5-dimethylcyclopentadienyl)zirconium dichloride; dimethylsilylene-bis(3-fluorophenylcyclopentadienyl)zirconium dichloride; dimethylsilylene-bis(4-fluorophenyl-2-methylcyclopentadienyl)zirconium dichloride, dimethylsilylene-bis(3-fluorophenyl-2-methylcyclopentadienyd)zirconium dichloride, dimethylsilylene-bis(3-naphthylcyclopentadienyl)zirconium dichloride, dimethylsilylene-bis(4-naphthyl-2-methylcyclopentadienyl)zirconium dichloride, dimethylsilylene-bis(3-naphthyl-2,5-dimethylcyclopentadienyl)zirconium dichloride; dimethylgemylene-bis(3-tolylcyclopentadienyl)zirconium dichloride, dimethylgermylene-bis(4-tolyl-2-methylcyclopentadienyl)zirconium dichloride, dimethylgermylene-bis(3-tolyl-2,5-dimethylcyclopentadienyl)zirconium dichloride; dimethylgermylene-bis(3-ethylphenylcyclopentadienyl)zirconium dichloride, dimethylgermylene-bis(4-ethylphenyl-2-methylcyclopentadienyl)zirconium dichloride, dimethylgermylene-bis(3-ethylphenyl-2,5-dimethylcyclopentadienyl)zirconium dichloride; dimethylgermylene-bis(3-fluorophenylcyclopentadienyl)zirconium dichloride, dimethylgermylene-bis(4-fluorophenyl-2-methylcyclopentadienyl)zirconium dichloride, dimethylgermylene-bis(3-fluorophenyl-2,5-dimethylcyclopentadienyl)zirconium dichloride; dimethylgermylene-bis(3-naphthylcyclopentadienyl)zirconium dichloride, dimethylgermylene-bis(4-naphthyl-2-methylcyclopentadienyl)zirconium dichloride, dimethylgermylene-bis(3-naphthyl-2,5-dimethylcyclopentadienyl)zirconium dichloride; dimethylsilylene-bis(3-tolylcyclopentadienyl)hafnium dichloride, dimethylsilylene-bis(4-tolyl-2-methylcyclopentadienyl)hafnium dichlorode, dimethylsilylene-bis(3-tolyl-2,5-dimethylcyclopentadienyl)hafnium dichloride; dimethylsilylene-bis(3-ethylphenylcyclopentadienyl)hafnium dichloride, dimethylsilylene-bis(4-ethylphenyl-2-methylcyclopentadienyl)hafnium dichloride, dimethylsilylene-bis(3-ethylphenyl-2,5-dimethylcyclopentadienyl)hafnium dichloride; dimethylsilylene-bis(3-fluorophenylcyclopentadienyl)hafnium dichloride, dimethylsilylene-bis(4-fluorophenyl-2-methylcyclopentadienyl)hafnium dichloride, dimethylsilylene-bis(3-fluorophenyl-2,5-dimethylcyclopentadienyl)hafnium dichloride; dimethylsilylene-bis(3-naphthylcyclopentadienyl)hafnium dichloride, dimethylsilylene-bis(4-naphthyl-2-methylcyclopentadienyl)hafnium dichloride, dimethylsilylene-bis(3-naphthyl-2,5-dimethylcyclopentadienyl)hafnium dichloride; dimethylgermylene-bis(3-tolylcyclopentadienyl)hafnium dichloride, dimethylgermylene-bis(4-tolyl-2-methylcyclopentadienyl)hafnium dichloride, dimethylgermylene-bis(3-tolyl-2,5-dimethylcyclopentadienyl)hafnium dichloride; dimethylgermylene-bis(3-ethylphenylcyclopentadienyl)hafnium dichloride, dimethylgermylene-bis(4-ethylphenyl-2-methylcyclopentadienyl)hafnium dichloride, dimethylgermylene-bis(3-ethylphenyl-2,5-dimethylcyclopentadienyl)hafnium dichloride; dimethylgermylene-bis(3-fluorophenylcyclopentadienyl)hafnium dichloride, dimethylgermylene-bis(4-fluorohyphenyl-2-methylcyclopentadienyl)hafnium dichloride, dimethylgermylene-bis(3-fluorophenyl-2,5-dimethylcyclopentadienyl)hafnium dichloride; dimethylgermylene-bis(3-naphthylcyclopentadienyl)hafnium dichloride, dimethylgermylene-bis(4-naphthyl-2-methylcyclopentadienyl)hafnium dichloride, dimethylgermylene-bis(3-naphthyl-2,5-dimethylcyclopentadienyl)hafnium dichloride; silacyclobutane-bis(3-tolylcyclopentadienyl)zirconium dichloride, silacyclobutane-bis(4-tolyl-2-methylcyclopentadienyl)zirconium dichloride, silacyclobutane-bis(3-tolyl-2,5-dimethylcyclopentadienyl)zirconium dichloride; silacyclobutane-bis(3-ethylphenylcyclopentadienyl)zirconium dichloride, silacyclobutane-bis(4-ethylphenyl-2-methylcyclopentadienyl)zirconium dichloride, silacyclobutane-bis(3-ethylphenyl-2,5-dimethylcyclopentadienyl)zirconium dichloride; silacyclobutane-bis(3-fluorophenylcyclopentadienyl)zirconium dichloride, silacyclobutane-bis(4-fluorophenyl-2-methylcyclopentadienyl)zirconium dichloride, silacyclobutane-bis(3-fluorophenyl-2,5-dimethylcyclopentadienyl)zirconium dichloride; silacyclobutane-bis(3-naphthylcyclopentadienyl)zirconium dichloride, silacyclobutane-bis(4-naphthyl-2-methylcyclopentadienyl)zirconium dichloride, silacyclobutane-bis(3-naphthyl-2,5-dimethylcyclopentadienyl)zirconium dichloride; silacyclobutane-bis(3-tolylcyclopentadienyl)hafnium dichloride, silacyclobutane-bis(4-tolyl-2-methylcyclopentadienyl)hafnium dichloride, silacyclobutane-bis(3-tolyl-2,5-dimethylcyclopentadienyl)hafnium dichloride; silacyclobutane-bis(3-ethylphenyicyclopentadienyl)hafnium dichloride, silacyclobutane-bis(4-ethylphenyl-2-methylcyclopentadienyl)hafnium dichloride, silacyclobutane-bis(3-ethylphenyl-2,5-dimethylcyclopentadienyl)hafnium dichloride; silacyclobutane-bis(3-fluorophen ylcyclopentadienyl)hafnium dichloride, silacyclobutane-bis(4-fluorophenyl-2-methylcyclopentadienyl)hafnium dichloride, silacyclobutane-bis(3-fluorophenyl-2,5-dimethylcyclopentadienyl)hafnium dichloride; silacyclobutane-bis(3-naphthylcyclopentadienyl)hafnium dichloride, silacyclobutane-bis(4-naphthyl-2-methylcyclopentadienyl)hafnium dichloride, silacyclobutane-bis(3-naphthyl-2,5-dimethylcyclopentadienyl)hafnium dichloride; silacyclopentane-bis(3-tolylcyclopentadienyl)zirconium dichloride, silacyclopentane-bis(4-tolyl-2- methylcyclopentadienyl)zirconium dichloride, silacyclopentane-bis(3-tolyl-2,5-dimethylcyclopentadienyl) zirconium dichloride; silacyclopentane-bis(3-ethylphenylcyclopentadienyl)zirconium dichloride, silacyclopentane-bis(4-ethylphenyl-2-methylcyclopentadienyl)zirconium dichloride, silacyclopentane-bis(3-ethylphenyl-2,5-dimethylcyclopentadienyl)zirconium dichloride; silacyclopentane-bis(3-fluorophenylcyclopentadienyl)zirconium dichloride, silacyclopentane-bis(4-fluorophenyl-2-methylcyclopentadienyl)zirconium dichloride, silacyclopentane-bis(3-fluorophenyl-2,5-dimethylcyclopentadienyl)zirconium dichloride; silacyclopentane-bis(3-naphthylcyclopentadienyl)zirconium dichloride, silacyclopentane-bis(4-naphthyl-2-methylcyclopentadienyl)zirconium dichloride, silacyclopentane-bis(3-naphthyl-2,5-dimethylcyclopentadienyl)zirconium dichloride; silacyclopentane-bis(3-tolylcyclopentadienyl)hafnium dichloride, silacyclopentane-bis(4-tolyl-2-methylcyclopentadienyl)hafnium dichloride, silacyclopentane-bis(3-tolyl-2,5-dimethylcyclopentadienyl) zirconium dichloride; silacyclopentane-bis(3-ethylphenylcyclopentadienyl)hafnium dichloride, silacyclopentane-bis(4-ethylphenyl-2-methylcyclopentadienyl)hafnium dichloride, silacyclopentane-bis(3-ethylphenyl-2,5-dimethylcyclopentadienyl)zirconium dichloride; silacyclopentane-bis(3-fluorophenylcyclopentadienyl)hafnium dichloride, silacyclopentane-bis(4-fluorophenyl-2-methylcyclopentadienyl)hafnium dichloride, silacyclopentane-bis(3-fluorophenyl-2,5-dimethylcyclopentadienyl)zirconium dichloride; silacyclopentane-bis(3-naphthylcyclopentadienyl)zirconium dichloride, silacyclopentane-bis(4-naphthyl-2-methylcyclopentadienyl)hafnium dichloride, silacyclopentane-bis(3-naphthyl-2,5-dimethylcyclopentadienyl)hafnium dichloride; dimethylsilylene-bis(tetrahydroindenyl)hafnium dichloride, dimethylsilylene-bis(2-methyltetrahydroindenyl)hafnium dichloride, dimethylsilylene-bis(indenyl)hafnium dichloride, dimethylsilylene-bis(2-methylindenyl)hafnium dichloride; dimethylsilylene-bis(2-methyl-4,5-benzoindenyl)hafnium dichloride, dimethylsilylene-bis(2-methyl-4-phenylindenyl)hafnium dichloride, dimethylsilylene-bis(2-methyl-4-naphthylindenyl)hafnium dichloride, dimethylsilylene-bis(1-cyclopentaphenanthryl)hafnium dichloride, dimethylsilylene-bis[1-(2-methylcyclopenta)phenanthryl]hafnium dichloride; dimethylgermylene-bis(tetrahydroindenyl)hafnium dichloride, dimethylgermylene-bis(2-methyltetrahydroindenyl)hafnium dichloride, dimethylgermylene-bis(indenyl)hafnium dichloride, dimethylgermylene-bis(2-methylindenyl)hafnium dichloride, dimethylgermylene-bis(2-methyl-4,5-benzoindenyl)hafnium dichloride, dimethylgermylene-bis(2-methyl-4-phenyhindenyl)hafnium dichloride, dimethylgermylene-bis(2-methyl-4-naphthylindenyl)hafnium dichloride, dimethylgermylene-bis(1-cyclopentaphenanthrylindenyl)hafnium dichloride, dimethylgermylene-bis[1-(2-methylcyclopenta)phenanthryl]hafnium dichloride; dimethylsilylene-bis(2-methyltetrahydroindenyl)zirconium dichloride, dimethylsilylene-bis(2-methylindenyl)zirconium dichloride, dimethylsilylene-bis(2-methyl-4,5-benzoindenyl)zirconium dichloride, dimethylsilylene-bis(2-methyl-4-phenylindenyl)zirconium dichloride, dimethylsilylene-bis(2-methyl-4-naphthylindenyl)zirconium dichloride, dimethylsilylene-bis[1-(2-methylcyclopent)phenanthryl]zirconium dichloride; dimethylgermylene-bis(2-methyltetrahydroindenyl)zirconium dichloride, dimethylgermylene-bis(2-methylindenyl)zirconium dichloride, dimethylgermylene-bis(2-methyl-4,5-benzoindenyl)zirconium dichloride, dimethylgermylene-bis(2-methyl-4-phenylindenyl)zirconium dichloride, dimethylgermylene-bis(2-methyl-4-naphthylindenyl)zirconium dichloride, dimethylgermylene-bis[1-(2-methylcyclopenta)phenanthryl]zirconium dichloride; dimethylsilylene-bis(2-methyltetrahydroindenyl)hafnium dichloride, dimethylsilylene-bis(2-methylindenyl)hafnium dichloride, dimethylsilylene-bis(2-methyl-4,5-benzoindenyl)hafnium dichloride, dimethylsilylene-bis(2-methyl-4-phenylindenyl)hafnium dichloride, dimethylsilylene-bis(2-methyl-4-naphthylindenyl)hafnium dichloride, dimethylsilylene-bis(1-(2-methylcyclopenta)phenanthryl)hafnium dichloride; dimethylgermylene-bis(2-methyltetrahydroindenyl)hafnium dichloride, dimethylgermylene-bis(2-methylindenyl)hafnium dichloride, dimethylgermylene-bis(2-methyl-4,5-benzoindenyl)hafnium dichloride, dimethylgermylene-bis(2-methyl-4-phenylindenyl)hafnium dichloride, dimethylgermylene-bis(2-methyl-4-naphthylindenyl)hafnium dichloride, dimethylgermylene-bis[1-(2-methylcyclopenta)phenanthryl]hafnium dichloride; dimethylsilylene-bis(2-ethyltetrahydroindenyl)zirconium dichloride, dimethylsilylene-bis(2-ethylindenyl)zirconium dichloride, dimethylsilylene-bis(2-ethyl-4,5-benzoindenyl)zirconium dichloride, dimethylsilylene-bis(2-ethyl-4-phenylindenyl)zirconium dichloride, dimethylsilylene-bis(2-ethyl-4-naphthylindenyl)zirconium dichloride, dimethylsilylene-bis[1-(2-ethylcyclopenta)phenanthryl]zirconium dichloride; dimethylgermylene-bis(2-ethyltetrahydroindenyl)zirconium dichloride, dimethylgermylene-bis(2-ethylindenyl)zirconium dichloride, dimethylgermylene-bis(2-ethyl-4,5-benzoindenyl)zirconium dichloride, dimethylgermylene-bis(2-ethyl-4-phenylindenyl)zirconium dichloride, dimethylgermylene-bis(2-ethyl-4-naphthylindenyl)zirconium dichloride, dimethylgermylene-bis[1-(2-ethylcyclopenta)phenanthryl]zirconium dichloride; dimethylsilylene-bis(2-ethyltetrahydroindenyl)hafnium dichloride, dimethylsilylene-bis(2-ethylindenyl)hafnium dichloride, dimethylsilylene-bis(2-ethyl-4,5-benzoindenyl)hafnium dichloride, dimethylsilylene-bis(2-ethyl-4-phenylindenyl)hafnium dichloride, dimethylsilylene-bis(2-ethyl-4-naphthylindenyl)hafnium dichloride, dimethylsilylene-bis[1-(2-ethylcyclopenta)phenanthryl]hafnium dichloride; dimethylgermylene-bis(2-ethyltetrahydroindenyl)hafnium dichloride, dimethylgermylene-bis(2-ethylindenyl)hafnium dichloride, dimethylgermylene-bis(2-ethyl-4,5-benzoindenyl)hafnium dichloride, dimethylgermylene-bis(2-ethyl-4-phenylindenyl)hafnium dichloride, dimethylgermylene-bis(2-ethyl-4-naphthylindenyl)hafnium dichloride, dimethylgermylene-bis[1-(2-ethylcyclopenta)phenanthryl] hafnium dichloride; dimethylsilylene-bis(2-isopropyltetrahydroindenyl)zirconium dichloride, dimethylsilylene-bis(2-isopropylindenyl)zirconium dichloride, dimethylsilylene-bis(2-isopropyl-4,5-benzoindenyl)zirconium dichloride, dimethylsilylene-bis(2-isopropyl-4-phenylindenyl)zirconium dichloride, dimethylsilylene-bis(2-isopropyl-4-naphthylindenyl)zirconium dichloride, dimethylsilylene-bis[1-(2-isopropylcyclopenta)phenanthryl]zirconium dichloride; dimethylgermylene-bis(2-isopropyltetrahydroindenyl)

zirconium dichloride, dimethylgermylene-bis(2-isopropylindenyl)zirconium dichloride, dimethylgermylene-bis(2-isopropyl-4,5-benzoindenyl)zirconium dichloride, dimethylgermylene-bis(2-isopropyl-4-phenylindenyl) zirconium dichloride, dimethylgermylene-bis(2-isopropyl-4-naphthylindenyl)zirconium dichloride, dimethylgermylene-bis[1-(2-isopropylcyclopenta) phenanthryl]zirconium dichloride; dimethylsilylene-bis(2-iso-propyltetrahydroindenyl)hafnium dichloride, dimethylsilylene-bis(2-isopropylindenyl)hafnium dichloride, dimethylsilylene-bis(2-isopropyl-4,5-benzoindenyl)hafnium dichloride, dimethylsilylene-bis(2-isopropyl-4-phenylindenyl)hafnium dichloride, dimethylsilylene-bis(2-isopropyl-4-naphthylindenyl) hafnium dichloride, dimethylsilylene-bis[1-(2-isopropylcyclopenta)phenanthryl]hafnium dichloride; dimethylgermylene-bis(2-isopropyltetrahydroindenyl) hafnium dichloride, dimethylgermylene-bis(2-isopropylindenyl)hafnium dichloride, dimethylgermylene-bis(2-isopropyl-4,5-benzoindenyl)hafnium dichloride, dimethylgermylene-bis(2-isopropyl-4-phenylindenyl) hafnium dichloride, dimethylgermylene-bis(2-isopropyl-4-naphthylindenyl)hafnium dichloride, dimethylgermylene-bis[1-(2-isopropylcyclopenta)phenanthryl]hafnium dichloride; tetramethylethylene-bis(3-tert-butylcyclopentadienyl)zirconium dichloride, tetramethylethylene-bis(4-tert-butyl-2-methylcyclopentadienyl)zirconium dichloride, tetramethylethylene-bis(3-tert-butyl-2,5-dimethylcyclopentadienyl)zirconium dichloride; tetramethylethylene-bis(3-phenylcyclopentadienyl) zirconium dichloride, tetramethylethylene-bis(4-phenyl-2-methylcyclopentadienyl)zirconium dichloride, tetramethylethylene-bis(3-phenyl-2,5-dimethylcyclopentadienyl)zirconium dichloride; tetramethylethylene-bis(tetrahydroindenyl)zirconium dichloride, tetramethylethylene-bis(indenyl)zirconium dichloride, tetramethylethylene-bis(2-methylindenyl) zirconium dichloride, tetramethylethylene-bis(2-methyl-4,5-benzoindenyl)zirconium dichloride, tetramethylethylene-bis(2-methyl-4-phenylindenyl)zircoum dichloride, tetramethylethylene-bis(2-methy-4-naphthylindenyl) zirconium dichloride, tetramethylethylene-bis(1-cyclopentaphenanthryl)zircomium dichloride, tetramethylethylene-bis[1-(2-methylcyclopenta) phenylindenyl)zirconium dichloride; tetramethylethylene-bis(3-tert-butylcyclopentadienyl)hafnium dichloride, tetramethylethylene-bis(4-tert-butyl-2-methylcyclopentadienyl)hafnium dichloride, tetramethylethylene-bis(3-tert-butyl-2,5-dimethylcyclopentadienyl)hafnium dichloride; tetramethylethylene-bis(3-phenylcyclopentadienyl)hafnium dichloride, tetramethylethylene-bis(4-phenyl-2-methylcyclopentadienyl)hafnium dichloride, tetramethylethylene-bis(3-phenyl-2,5-dimethylcyclopentadienyl)hafnium dichloride; tetramethylethylene-bis(tetrahydroindenyl)hafnium dichloride, tetramethylethylene-bis(indenyl)hafnium dichloride, tetramethylethylene-bis(2-methylindenyl) hafnium dichloride, tetramethylethylene-bis(2-methyl-4,5-benzoindenyl)hafnium dichloride, tetramethylethylene-bis(2-methyl-4-phenylindenyl)hafnium dichloride, tetramethylethylene-bis(2-methyl-4-naphthylindenyl) hafnium dichloride, tetramethylethylene-bis(1-cyclopentaphenanthryl)hafnium dichloride, tetramethylethylene-bis[1-(2-methylcyclopenta) phenanthryl]hafnium dichloride; tetramethyidisilane-bis(3-tert-butylcyclopentadienyl)zirconium dichloride, tetramethyldisilane-bis(4-tert-butyl-2-methylcyclopentadienyl)zirconium dichloride, tetramethyldisilane-bis(3-tert-butyl-2,5-dimethylcyclopentadienyl)zirconium dichloride; tetramethyldisilane-bis(3-phenylcyclopentadienyl) zirconium dichloride, tetramethyldisilane-bis(4-phenyl-2-methylcyclopentadienyl)zirconium dichloride; tetramethyldisilane-bis(3-phenyl-2,5-dimethylcyclopentadienyl)zirconium dichloride; tetramethyldisilane-bis(tetrahydroindenyl)zirconium dichloride, tetramethyldisilane-bis(indenyl)zirconium dichloride, tetramethyldisilane-bis(2-methylindenyl) zirconium dichloride, tetramethyldisilane-bis(2-methyl-4,5-benzoindenyl)zirconium dichloride, tetramethyldisilane-bis(2-methyl-4-phenylindenyl)zirconium dichloride, tetramethyldisilane-bis(2-methyl-4-naphthylindenyl) zirconium dichloride, tetramethyldisilane-bis(1-cyclopentaphenanthryl)zirconium dichloride, tetramethyldisilane-bis[1-(2-methylcyclopentaphenanthryl] zirconium dichoride; tetramethyldisilane-bis(3-tert-butylcyclopentadienyl)hafnium dichloride, tetramethyldisilane-bis(4-tert-butyl-2-methylcyclopentadienyl)hafnium dichloride, tetramethyldisilane-bis(3-tert-butyl-2,5-dimethylcyclopentadienyl)hafnium dichloride; tetramethyldisilane-bis(3-phenylcyclopentadienyl)hafnium dichloride, tetramethyldisilane-bis(4-phenyl-2-methylcyclopentadienyl)hafnium dichloride, tetramethyldisilane-bis(3-phenyl-2,5-dimethylcyclopentadienyl)hafnium dichloride; tetramethyldisilane-bis(tetrahydroindenyl)hafnium dichloride, tetramethyldisilane-bis(indenyl)hafnium dichloride, tetramethyldisilane-bis(2-methylindenyl) hafnium dichloride, tetramethyldisilane-bis(2-methyl-4,5-benzoindenyl)hafnium dichloride, tetramethyldisilane-bis(2-methyl-4-phenyindenyl)hafnium dichloride, tetramethyldisilane-bis(2-methyl-4-naphthylindenyl) hafnium dichloride, tetramethyldisilane-bis(1-cyclopentaphenanthryl)hafnium dichloride, tetramethyldisilane-bis [1-(2-cyclopenta)phenanthryl] hafnium dichloride; diphenylsilylene-bis(3-tert-butylcyclopentadienyl)zirconium dichloride, diphenylsilylene-bis(4-tert-butyl-2-methylcyclopentadienyl)zirconium dichloride, diphenylsilylene-bis(3-tert-butyl-2,5-dimethylcyclopentadienyl)zirconium dichloride; diphenylsilylene-bis(3-phenylcyclopentadienyl)zirconium dichloride, diphenylsilylene-bis(4-phenyl-2-methylcyclopentadienyl)zirconium dichloride, diphenylsilylene-bis(3-phenyl-2,5-dimethylcyclopentadienyl)zirconium dichloride; diphenylsilylene-bis(3-ethylphenyl-2-methylcyclopentadienyl)zirconium dichloride, diphenylsilylene-bis(4-ethylphenyl-2-methylcyclopentadienyl)zirconium dichloride, diphenylsilylene-bis(3-ethylphenyl-2,5-dimethylcyclopentadienyl)zirconium dichloride; diphenylsilylene-bis(3-fluorophenylcyclopentadienyl) zirconium dichloride, diphenylsilylene-bis(4-fluorophenyl-2-methylcyclopentadienyl)zirconium dichloride, diphenylsilylene-bis(3-fluorophenyl-2,5-dimethylcyclopentadienyl)zirconium dichloride; diphenylsilylene-bis(3-naphthylcyclopentadienyl)zirconium dichloride, diphenylsilylene-bis(4-naphthyl-2-methylcyclopentadienyl)zirconium dichloride, diphenylsilylene-bis(3-napphthyl-2,5- dimethylcyclopentadienyl)zirconium dichloride; diphenylsilylene-bis(tetrahydroindenyl)zirconium dichloride, diphenylsilylene-bis(indenyl)zirconium dichloride, diphenylsilylene-bis(2-methylindenyl)zirconium dichloride, diphenylsilylene-bis(2-methyl-4,5-benzoindenyl)zirconium dichloride, diphenylsilylene-bis(2-methyl-4-phenylindenyl)zirconium dichloride, diphenylsilylene-bis(2-methyl-4-naphthylindenyl)zirconium dichloride, diphenylsilylene-bis(1-cyclopentaphenanthryl)zirconium dichloride, diphenylsilylene-bis[1-(2-cyclopenta)phenanthryl]zirconium dichloride; diphenylsilylene-bis(3-tert-butylcyclopentadienyl)hafnium dichloride, diphenylsilylene-bis(4-tert-butyl-2-methylcyclopentadienyl)hafnium dichloride, diphenylsilylene-bis(3-tert-butyl-2,5-dimethylcyclopentadienyl)hafnium dichloride; diphenylsilylene-bis(3-phenylcyclopentadienyl)hafnium dichloride, diphenylsilylene-bis(4-phenyl-2-methylcyclopentadienyl)hafnium dichloride, diphenylsilylene-bis(3-phenyl-2,5-dimethylcyclopentadienyl)hafnium dichloride; diphenylsilylene-bis(3-ethylphenylcyclopentadienyl)hafnium dichloride, diphenylsilylene-bis(4-ethylphenyl-2-methylcyclopentadienyl)hafnium dichloride, diphenylsilylene-bis(3-ethylphenyl-2,5-dimethylcyclopentadienyl)hafnium dichloride; diphenylsilylene-bis(3-fluorophenylcyclopentadienyl)hafnium dichloride, diphenylsilylene-bis(4-fluorophenyl-2-methylcyclopentadienyl)hafnium dichloride, diphenylsilylene-bis(3-fluorophenyl-2,5-dimethylcyclopentadienyl)hafnium dichloride; diphenylsilylene-bis(3-naphthylcyclopentadienyl)hafnium dichloride, diphenylsilylene-bis(4-naphthyl-2-methylcyclopentadienyl)hafnium dichloride, diphenylsilylene-bis(3-naphthyl-2,5-dimethylcyclopentadienyl)hafnium dichloride; diphenylsilylene-bis(tetrahydroindenyl)hafnium dichloride, diphenylsilylene-bis(indenyl)hafnium dichloride, diphenylsilylene-bis(2-methylindenyl)hafnium dichloride, diphenylsilylene-bis(2-methyl-4,5-benzoindenyl)hafnium dichloride, diphenylsilylene-bis(2-methyl-4-phenylindenyl)hafnium dichloride, diphenylsilylene-bis(2-methyl-4-naphthylindenyl)hafnium dichloride, diphenylsilylene-bis(1-cyclopentaphenanthryl)hafnium dichloride, diphenylsilylene-bis[1--(2-methylcyclopenta)phenanthryl]hafnium dichloride; methylphenylsilylene-bis(3-tert-butylcyclopentadienyl)zirconium dichloride, methylphenylsilylene-bis(4-tert-butyl-2-methylcyclopentadienyl)zirconium dichloride, methylphenylsilylene-bis(3-tert-butyl-2,5-dimethylcyclopentadienyl)zirconium dichloride; methylphenylsilylene-bis(3-phenylcyclopentadienyl)zirconium dichloride, methylphenylsilylene-bis(4-phenyl-2-methylcyclopentadienyl)zirconium dichloride, methylphenylsilylene-bis(3-phenyl-2,5-dimethylcyclopentadienyl)zirconium dichloride; methylphenylsilylene-bis(3-ethylphenylcyclopentadienyl)zirconium dichloride, methylphenylsilylene-bis(4-ethylphenyl-2-methylcyclopentadienyl)zirconium dichloride, methylphenylsilylene-bis(3-ethylphenyl-2,5-diethylcyclopentadienyl)zirconium dichloride; methylphenylsilylene-bis(3-fluorophenyicyclopentadienyl)zirconium dichloride, methylphenylsilylene-bis(4-fluorophenyl-2-methylcyclopentadienyl)zirconium dichloride, methylphenylsilylene-bis(3-fluorophenyl-2,5-dimethylcyclopentadienyl)zirconium dichloride; methylphenylsilylene-bis(3-naphthylcyclopentadienyl)zirconium dichloride, methylphenylsilylene-bis(4-naphthyl-2-methylcyclopentadienyl)zirconium dichloride, methylphenylsilylene-bis(3-naphthyl-2,5-dimethylcyclopentadienyl)zirconium dichloride; methylphenylsilylene-bis(tetrahydroindenyl)zirconium dichloride, methylphenylsilylene-bis(indenyl)zirconium dichloride, methylphenylsilylene-bis(2-methylindenyl)zirconium dichloride, methylphenylsilylene-bis(2-methyl-4,5-benzoindenyl)zirconium dichloride, methylphenylsilylene-bis(2-methyl-4-phenylindenyl)zirconium dichloride, methylphenylsilylene-bis(2-methyl-4-naphthylindenyl)zirconium dichloride, methylphenylsilylene-bis(1-cyclopentaphenanthryl)zirconium dichloride, methylphenylsilylene-bis[1-(2-cyclopenta)phenanthryl]zirconium dichloride; methylphenylsilylene-bis(3-tert-butylcyclopentadienyl)hafnium dichloride, methylphenylsilylene-bis(4-tert-butyl-2-methylcyclopentadienyl)hafnium dichloride, methylphenylsilylene-bis(3-tert-butyl-2,5-dimethylcyclopentadienyl)hafnium dichloride; methylphenylsilylene-bis(3-phenylcyclopentadienyl)hafnium dichloride, methylphenylsilylene-bis(4-phenyl-2-methylcyclopentadienyl)hafnium dichloride, methylphenylsilylene-bis(3-phenyl-2,5-dimethylcyclopentadienyl)hafnium dichloride; methylphenylsilylene-bis(3-ethylphenylcyclopentadienyl)hafnium dichloride, methylphenylsilylene-bis(4-ethylphenyl-2-methylcyclopentadienyl)hafnium dichloride; methylphenylsilylene-bis(3-ethylphenyl-2,5-dimethyiyclopentadienyl)hafnium dichloride; methylphenylsilylene-bis(3-fluorophenylcyclopentadyl)hafnium dichloride, methylphenylsilylene-bis(4-fluorophenyl-2-methylcyclopentadienyl)hafniunm dichloride, methylphenylsilylene-bis(3-fluorophenyl-2,5-dimethycyclopentadienyl)hafnium dichloride; methylphenylsilylene-bis(3-naphthylcyclopentadienyl)hafnium dichloride; methylphenylsilylene-bis(4-naphthyl-2-methylcyclopentadienyl)hafnium dichloride, methylphenylsilylene-bis(3-naphthyl-2,5-dimethylcyclopentadienyl)hafnium dichloride; methylphenylsilylene-bis(tetrahydroindenyl)hafnium dichloride, methylphenylsilylene-bis(indenyl)hafnium dichloride, methylphenylsilylene-bis(2-methytindenyl)hafnium dichloride, methylphenylsilylene-bis(2-methyl-4,5-bentadioenyl)hafnium dichloride, methylphenylsilylene-bis(2-methyl-4-phenylindenyl)hafnium dichloride; methylphenylsilylene-bis(2-methyl-4-naphthyindenyl)hafnium dichloride, methylphenylsilylene-bis(1-cyclopentaphenanthryl)hafnium dichloride, methylphenylsilylene-bis[(1-(2-cyclopenta)phenanthryl]hafnium dichloride; diphenylgermylene-bis(3-tert-butylcyclopentadienyl)zirconium dichloride, diphenylgermylene-bis(4-tert-butyl-2-methylcyclopentadienyl)zirconium dichloride, diphenylgermylene-bis(3-tert-butyl-2,5-dimethylcyclopentadienyl)zirconium dichloride; diphenylgermylene-bis(3-phenylcyclopentadienyl)zirconium dichloride, diphenylgermylene-bis(4-phenyl-2-methylcyclopentadienyl)zirconium dichloride, diphenylgermylene-bis(3-phenyl-2,5-dimethylcyclopentadienyl)zirconium dichloride; diphenylgermylene-bis(3-ethylphenylcyclopentadienyl)zirconium dichloride, diphenylgermylene-bis(4-ethylphenyl-2-methylcyclopentadienyl)zirconium dichloride, diphenylgermylene-bis(3-ethylphenyl-2,5-dimethylcyclopentadienyl)zirconium dichloride;

diphenylgermylene-bis(3-fluorophenylcyclopentadienyl) zirconium dichloride, diphenylgermylene-bis(4-fluorophenyl-2-methylcyclopentadienyl)zirconium dichloride, diphenylgermylene-bis(3-fluorophenyl-2,5-dimethylcyclopentadienyl)zirconium dichloride; diphenylgermylene-bis(3-naphthylcyclopentadienyl) zirconium dichloride, diphenylgermylene-bis(4-lenaphthyl-2-methylcyclopentadienyl)zirconium dichloride, diphenylgermylene-bis(3-naphthyl-2,5-dimethylcyclopentadienyl)zirconium dichloride; diphenylgermylene-bis(tetrahydroindenyl)zirconium dichloride, diphenylgermylene-bis(indenyl)zirconium dichloride, diphenylgermylene-bis(2-methylindenyl) zirconium dichloride, diphenylgermylene-bis(2-methyl-4,5-benzoindenyl)zirconium dichloride, diphenylgermylene-bis(2-methy-4-phenyllindenyl)zirconium dichloride, diphenylgermylene-bis(2-methyl-4-naphthylindenyl) zirconium dichloride, diphenylgermylene-bis(1-cyclopentaphenanthryl)zirconium dichloride, diphenylgermylene-bis[1-(2-methylcyclopenta) phenanthryl]zirconium dichloride; diphenylgermylene-bis (3-tert-butylcyclopentadienyl)hafnium dichloride, diphenylgermylene-bis(4-tert-butyl-2-methylcyclopentadienyl)hafnium dichloride, diphenylgermylene-bis(3-tert-butyl-2,5-dimethylcyclopentadienyl)hafnium dichloride; diphenylgermylene-bis(3-phenylcyclopentadienyl)hafnium dichloride, diphenylgermylene-bis(4-phenyl-2-methylcyclopentadienyl)hafnium dichloride, diphenylgermylene-bis(3-phenyl-2,5-dimethylcyclopentadienyl)hafnium dichloride; diphenylgermylene-bis(3-ethylphenylcyclopentadienyl) hafnium dichloride, diphenylgermylene-bis(4-ethylphenyl-2-methylcyclopentadienyl)hafnium dichloride, diphenylgermylene-bis(3-ethylphenyl-2,5-dimethylcyclopentadienyl)hafnium dichlioride; diphenylgermylene-bis(3-fluorophenylcyclopentadienyl) hafnium dichloride, diphenylgermylene-bis(4-fluorophenyl-2-methylcyclopentadienyl)hafnium dichloride, diphenylgennylene-bis(3-fluorophenyl-2,5-dimethylcyclopentadienyl)hafnium dichloride; diphenylgermylene-bis(3-naphthylcyclopentadienyl) hafnium dichloride, diphenylgermylene-bis(4-naphthyl-2-methylcyclopentadienyl)hafnium dichloride, diphenylgermylene-bis(3-naphthyl-2,5-dimethylcyclopentadienyl)hafnium dichloride; diphenylgermylene-bis(tetrahydroindenyl)hafnium dichloride, diphenylgermylene-bis(indenyl)hafnium dichloride, diphenylgermylene-bis(2-methylindenyl) hafnium dichloride, diphenylgermylene-bis(2-methyl-4,5-benzoindenyl)hafnium dichloride, diphenylgermylene-bis (2-methyl-4-phenylindenyl)hafnium dichloride, diphenylgermylene-bis(2-methyl-4-naphthylindenyl) hafnium dichloride, diphenylgermylene-bis(1-cyclopentaphenanthryl)hafnium dichoride, diphenylgermylene-bis[1-(2-cyclopenta)phenanthryl] hafnium dichoride; methylphenylgermylene-bis(3-tert-butylcyclopentadienyl)zirconium dichloride, methylphenylgermylene-bis(4-tert-butyl-2-methylcyclopentadienyl)zirconium dichloride, methylphenylgermylene-bis(3-tert-butyl-2,5-dimethyldichloride; methylphenylgermylene-bis(3-phenylcyclopentadienyl)zirconium dichloride, methylphenylgermylene-bis(4-phenyl-2-methylcyclopentadienyl)zirconium dichloride, methylphenylgermylene-bis(3-phenyl-2,5-dimethylcyclopentadienyl)zirconium dichloride; methylphenylgermylene-bis(3-ethylphenylcyclopentadienyl)zirconium dichloride, methylphenylgermylene-bis(4-ethylphenyl-2-methylcyclopentadienyl)zirconium dichloride, methylphenylgermylene-bis(3-ethylphenyl-2,5-dimethylcyclopentadienyl)zirconium dichloride; methylphenylgermylene-bis(3-fluorophenylcyclopentadienyl)zirconium dichloride, methylphenylgermylene-bis(4-fluorophenyl-2-methylcyclopentadienyl)zirconium dichloride, methylphenylgermylene-bis(3-fluorophenyl-2,5-dimethylcyclopentadienyl)zirconium dichloride; methylphenylgermylene-bis(3-naphthylcyclopentadienyl) zirconium dichloride, methylphenylgermylene-bis(4-naphthyl-2-methylcyclopentadienyl)zirconium dichloride, methylphenylgermylene-bis(3-naphthyl-2,5-dimethylcyclopentadienyl)zirconium dichloride; methylphenylgermylene-bis(tetrahydroindenyl)zirconium dichloride, methylphenylgermylene-bis(indenyl)zirconium dichloride, methylphenylgermylene-bis(2-methylindenyl) zirconium dichloride, methylphenylgermylene-bis(2-methyl-4,5-benzoindenyl)zirconium dichloride, methylphenylgermylene-bis(2-methy-4-phenylindenyl) zirconium dichloride, methylphenylgermylene-bis(2-methyl-4-naphtylindenyl)zirconium dichloride, methylphenylgermylene-bis(1-cyclopentaphenanthryl) zirconium dichloride, methylphenylgermylene-bis[1-(2-cyclopenta)phenanthryl]zirconium dichloride; methylphenylgermylene-bis(3-tert-butylcyclopentadienyl) hafnium dichloride, methylphenylgermylene-bis(4-tert-butyl-2-methylcyclopentadienyl)hafnium dichloride, methylphenylgermylene-bis(3-tert-butyl-2,5-dimethylmethylcyclopentadienyl)hafnium dichloride; methylphenylgermylene-bis(3-phenylcyclopentadienyl) hafnium dichloride; methylphenylgermylene-bis(3-phenyl-2-methylcyclopentadienyl)hafnium dichloride, methylphenylgermylene-bis(3-phenyl-2, 5dimethyllcyclopentadienyl)hafnium dichloride, methylphenylgermylene-bis(3-ethylphenyicyclopentadienyl)hafnium dichloride, methylphenylgermylene-bis(4-ethylphenyl-2-methylcyclopentadienyl)hafnium dichloride, methylphenylgermylene-bis(3-ethylphenyl-2,5-dimethylcyclopentadienyl)hafnium dichloride; methylphenylgermylene-bis(3-ethylphenylcyclopentadienyl)hafnium dichloride, methylphenylgermylene-bis(4-ethylphenyl-2-methylcyclopentadienyl)hafnium dichloride, methylphenylgermylene-bis(3-ethylphenyl -2,5-dimethylcyclopenadienyl)hafnium dichloride; methylphenylgermylene-bis(3-fluorophenylcyclopentadienylhafnium dichloride, methylphenylgermylene-bis(4-fluorophenyl-2-methylcyclopentadienyl)hafnium dichloride, methylphenylgermylene-bis(3-fluorophenyl-2,5-dimethylcyclopentadienyl)hafnium dichloride; methylphenylgermylene-bis(3-naphthylcyclopentadienyl) hafnium dichloride, methylphenylgermylene-bis(4-naphthyl-2-methylcyclopentadienyl)hafnium dichloride, methylphenylgermylene-bis(3- naphthyl-2,5-ddimethylcyclopentadienyl)hafnium dichloride; methylphenylgermylene-bis(tetrahydroindenyl)hafnium dichloride, methylphenylgermylene-bis(indenyl)hafnium dichloride, methylphenylgermylene-bis(2-methylindenyl) hafnium dichloride, methylphenylgermylene-bis(2-methyl-4,5-benzoindenyl)hafnium dichloride, methylphenylgermylene-bis(2-methyl-4-phenylindenyl)

hafnium dichloride, methylphenylgermylene-bis(2-methyl-4-naphthylindenyl)hafnium dichloride, methylphenylgermylene-bis(1-cyclopentaphenanthryl)hafnium dichloride, methylphenylgermylene-bis[1-(2-cyclopenta)phenanthryl]hafnium dichloride; dimethylsilylene-bis[2-(2-furyl)-3,5-dimethylcyclopentadienyl]zirconium dichloride, dimethylsilylene-bis[2-(2-furyl)-4,5-dimethylcyclopentadienyl]zirconium dichloride, dimethylsilylene-bis[2-(2-furyl)-indenyl]zirconium dichloride, dimethylsiltlene-bis[2-(2-benzofuryl)-3,5-dimethylcyclopentadienyl]zirconium dichloride, dimethylsilylene-bis[2-(2-benzofuryl)-4,5-dimethylcyclopentadienyl]zirconium dichloride, dimethylsilylene-bis[2-(2-benzofuryl)indenyl]zirconium dichloride, dimethylsilylene-bis(2-methyl-4-phenyl-4-hydroazulenyl)zirconium dichloride, and dimethylsilylene-bis(2-methyl-4-phenyl-4-hydroazulenyl)hafnium dichloride.

EXAMPLES

The present invention will now be illustrated in more detail by way of Examples.

In Examples, all of the reactions was carried out in an inert gas atmosphere. Reagents and solvents used in syntheses are wholly those available commercially and actually employed without any dehydrating treatment, while the reagents and solvents used for polymerization were previously dried.

Example 1
[Synthesis of racemic-dimethylsilylene-bis(2,3,5-trimethylcyclopentadienyl)zirconium dichloride]

In a 500 ml reaction vessel made of glass were placed 4.6 g (11 mmole) of an isomeric mixture of dimethylsilylene-bis(2,3,5-trimethylcyclopentadienyl)zirconium dichloride (the racemic form/the meso form=50/50) and 170 ml of toluene, and the content was cooled down to −10° C. in a dry ice-methanol bath. To the mixture was added dropwise a solution of 0.46 g (6 mmole) of diethylamine in 20 ml of toluene, and then added 0.5 g (3 mmole) of water.

The dry ice-methanol bath was removed and the mixture was stirred as such for 18 hours at room temperature. An NMR analysis was carried out whereby it was confirmed that a peak of the meso form disappeared. The solvent was removed under reduced pressure and 30 ml of toluene and 30 ml of hexane were added to the residue, and the mixture was stirred for one hour at 60° C. and then filtered. The $\mu$-oxo-complex and the racemic form as filtration residue were 80/20 in weight ratio. The diethylamine hydrochloride was contained in the filtration residue.

The $\mu$-oxo-complex was identified by way of an NMR analysis, elementary analysis and single crystal X-ray diffration and its structure was also determined. A result of an NMR analysis and an elementary analysis of the $\mu$-oxo-complex is shown in Table 1.

The filtrate ($\mu$-oxo-complex/the racemic form=20/80) was cooled to −20° C. and allowed to stand for one day. The precipitated crystals were collected by filtration, washed with hexane and dried whereby racemic-dimethylsilylyene-bis(2,3,5-trimethylcyclopentadienyl)zirconium dichloride was obtained as light yellow crystals (purity: at least 99%; 0.87 g, Yield: 40%).

Example 2
[Synthesis of dimethylsilylene-bis(2,3,5-trimethylcyclopentadienyl)zirconium dichloride]

In a 100 ml reaction vessel made of glass were placed 210 mg (0.5 mmole) of an isomeric mixture of dimethylsilylene-bis(2,3,5-trimethylcyclopentadienyl)zirconium dichloride (the racemic form/the meso form=50/50) and 20 ml of toluene. To the mixture was added dropwise a solution of 0.5 ml (0.25 mmol) of triethylamine (0.5 mol/l) in toluene at room temperature. It was found that a ratio of the racemic form to the meso form was 75/15 according to an NMR analysis. The solvent was concentrated under reduced pressure, and 50 ml of hexane was added to the mixture which was then allowed to stand overnight and filtered. The filtered residue was 98 mg and it was $\mu$-oxo-complex and triethylamine hydrochloride.

The solvent of the filtrate was distilled off under reduced pressure, and toluene was added to dissolve the residue, and thereafter hexane was added, cooled down to −20° C. and allowed to stand for one day. The precipitated crystals were collected by filtration, washed with hexane and dried to obtain 90 mg (yield: 43%) of dimethylsilylene-bis(2,3,5-trimethylcyclopentadienyl)zirconium dichloride (the recemic form/the meso form=90/10) as light yellow crystals.

Example 3
[Synthesis of silacyclopentane-bis(2,3,5-trimethylcyclopentadienyl)zirconium dichloride]

In a 100 ml reaction vessel made of glass were placed 190 mg (0.44 mmole) of an isomeric mixture of silacyclopentane-bis(2,3,5-trimethylcyclopentadienyl)zirconium dichloride (the racemic form/the meso form=40/60) and 20 ml of toluene. To the mixture was added dropwise 0.55 ml (0.5 mol/l) of a solution of 0.5 ml (0.44 mmol) of diethylamine in toluene at room temperature. It was confirmed that a ratio of the racemic form to the meso form was 93/7 according to an NMR analysis.

The solvent was concentrated under reduced pressure, and 50 ml of hexane was added to the mixture which was then allowed to stand overnight and filtered. The residue on the filter was 80 mg and it was $\mu$-oxo-complex and diethylamine hydrochloride. A result of an NMR analysis and elementary analysis of the $\mu$-oxo-complex was shown in Table 1. A single crystal X-ray diffraction test was also carried out to determine the structure thereof.

The solvent of the filtrate was distilled off under reduced pressure, and toluene was added to dissolve the residue, and thereafter hexane was added, cooled down to −20° C. and allowed to stand for one day. The precipitated crystals were collected by filtration, washed with hexane and dried to obtain 9 mg (yield: 5%) of silacyclopentane-bis(2,3,5-timethylcyclopentadienyl)zirconium dichloride (the recemic form/the meso form=97/3) as light yellow crystals.

Example 4
[Synthesis of dimethylsilylene-bis(3-tert-butylcyclopentadienyl)zirconium dichloride]

In a 100 ml reaction vessel made of glass were placed 230 mg (0.5 mmole) of dimethylsilylene-bis(3-tert-butylcyclopentadienyl)zirconium dichloride (the racemic form/the meso form=40/60) and 20 ml of toluene. To the mixture was added dropwise 0.55 ml (0.5 mole/l) of a solution of 0.5 ml (0.25 mmole) of triethylamine in toluene at room temperature. It was confirmed that a ratio of the racemic form to the meso form was 68/32 according to an NMR analysis.

The solvent was concentrated under reduced pressure, and 50 ml of hexane was added to the mixture which was then allowed to stand overnight and filtered. The residue on the filter was 63 mg and it was an μ-oxo-complex and triethylamine hydrochloride. A result of an NMR analysis and elementary analysis of the μ-oxo-complex was shown in Table 1.

The solvent of the filtrate was distilled off under reduced pressure, and toluene was added to dissolve the residue, and thereafter hexane was added, cooled down to −20° C. and allowed to stand for one day. The precipitated crystals were collected by filtration, washed with hexane and dried to -obtain 60 mg (yield: 26%) of dimethylsilylene-bis(3-tert-butylcyclopentadienyl)zirconium dichloride (the recemic form/the meso form=70/30) as light yellow crystals.

Example 5
[Synthesis of dimethylgermylene-bis(2,3,5-trimethylcyclopentadienyl)zirocnium dichloride]

In a 100 ml reaction vessel made of glass were placed 240 mg (0.5 mmole) of an isomric mixture (the racemic form/the meso form=50/50) of dimethylgermylene-bis(2,3,5-trimethylcyclopentadienyl)zirconium dichloride and 20 ml of toluene. To the mixture was added dropwise 0.5 ml (0.25 mole/l) of a solution of 0.5 ml/l) of triethylamine in toluene at room temperature. It was confirmed that a ratio of the racemic form to the meso form was 87/13 according to an NMR analysis.

The solvent was concentrated under reduced pressure, and 50 ml of hexane was added to the mixture which was then allowed to stand overnight and filtered. The residue on the filter was 71 mg and it was an μ-oxo-complex and triethylamine hydrochloride. A result of an NMR analysis and elementary analysis of the μ-oxo-complex was shown in Table 1.

The solvent of the filtrate was distilled off under reduced pressure, and toluene was added to dissolve the residue, and thereafter hexane was added, cooled down to −20° C. and allowed to stand for one day. The precipitated crystals were collected by filtration, washed with hexane and dried to obtain 31 mg (yield: 13%) of dimethylgermylene-bis(2,3,5-trimethylcyclopentadienyl)zirconium dichloride (the recemic form/the meso form=90/10) as light yellow crystals.

Example 6
[Synthesis of dimethylgermylene-bis(2,3,5-trimethylcyclopentadienyl)hafnium dichloride]

In a 100 ml reaction vessel made of glass were placed 280 mg (0.5 mmole) of an isomric mixture (the racemic form/the meso form=50/50) of dimethylgermylene-bis(2,3,5-trimethylcyclopentadienyl)hafnium dichloride and 20 ml of toluene. To the mixture was added dropwise 0.5 ml (0.25 mole/l) of a solution of 0.5 ml/l) of triethylamine in toluene at room temperature. It was confirmed that a ratio of the racemic form to the meso form was 68/32 according to an NMR analysis.

The solvent was concentrated under reduced pressure, and 50 ml of hexane was added to the mixture which was then allowed to stand overnight and filtered. The residue on the filter was 51 mg and it was triethylamine hydrochloride.

The solvent of the filtrate was distilled off under reduced pressure, and toluene was added to dissolve the residue, and thereafter hexane was added, cooled down to −20° C. and allowed to stand overnight. The precipitated crystals was collected by filtration. The resultant crystals were 6 mg of the μ-oxo-complex. A result of an NMR analysis and elementary analysis of the μ-oxo-complex was shown in Table 1.

The solvent of the filtrate was distilled off under reduced pressure, and toluene was added to dissolve the residue, and thereafter hexane was added, cooled down to −20° C. and allowed to stand for one day. The precipitated crystals were collected by filtration, washed with hexane and dried to obtain 40 mg (yield: 7%) of dimethylgermylene-bis(2,3,5-trimethylcyclopentadienyl)hafnium dichloride (the racemic form/the meso form=87/13) as light yellow crystals.

A result of an NMR analysis and elementary analysis of the μ-oxo-complex was shown in Table 1.

Example 7
[Synthesis of racemic-dimethylsilylene-bis[2-(2-furyl)-3,5-dimethylcyclopentadienyl]zirconium dichloride]

In a 100 ml reaction vessel made of glass were placed 460 mg (0.86 mmole) of an isomric mixture (the racemic form/the meso form=77/23) of dimethylsilylene-bis[2-(2-furyl)-3,5-dimethylcyclopentadienyl]zirconium dichloride and 20 ml of toluene. To the mixture was added dropwise 0.73 ml (0.12 mole/l) of a solution of 0.277 mol/l) of triethylamine in toluene at room temperature, and the mixture was stirred as such for 18 hours.

The solvent was concentrated under reduced pressure, and 10 ml of toluene was added to the mixture which was then allowed to stand overnight and filtered. The residue on the filter was an μ-oxo-complex and triethylamine hydrochloride.

The solvent of the filtrate was distilled off under reduced pressure, and toluene was added to dissolve the residue, and thereafter hexane was added, cooled down to −20° C. and allowed to stand for one day. The precipitated crystals were collected by filtration, washed with hexane and dried to obtain 170 mg (yield: 37%) of dimethylsilylene-bis[2-(2-furyl)-3,5-dimethylcyclopentadienyl]zirconium dichloride (the recemic form/the meso form=97/3) as light yellow crystals. A result of an NMR measurement and an elementary analysis of the μ-oxo-complex is shown in Table 1.

Comparative Example 1
[Synthesis of dimethylsilylene-bis(2,3,5-trimethylcyclopentadienyl)zirconium dichloride]

In a 1000 ml reaction vessel made of glass was placed 11.0 g (25 mmole) of an isomeric mixture (the racemic form/the meso form=53/47) of dimethylsilylene-bis(2,3,5-trimethylcyclopentadienyl)zirconium dichloride, and 290 ml of toluene was added to dissolve the mixture completely. To the solution was further added 400 ml of hexane, and the solution was cooled to 5° C. and then allowed to stand for one day. The precipitated crystals were collected by filtration, washed with hexane and dried to obtain 1.6 g (yield: 15%) of dimethylsilylene-bis(2,3,5-trimethylcyclopentadienyl)zirconium dichloride (the racemic form/the meso form=65/35) as light yellow crystals.

Industrial Utilizability

According to the present invention, there can be provided a process for the preparation of metilocene complexes capable of easily increasing purity of the isomers. Thus, isomers of a high purity can now be obtained. In particular, the purity of the racemic form can easily be enhanced, starting from a mixture of the racemic form and the meso form so that the racemic form of a high purity can now be obtained.

This is indeed a technical effect never achievable by a prior art conventional production process wherein an ordinary separation method such as recrystallization or extraction is carried out.

TABLE 1

Analytical data of the μ-oxo complex compounds

| | $^1$H-NMR Spectra (CDCl$_3$; ppm) | Elementary Analysis (wt. %) | |
|---|---|---|---|
| | | Calc. | Found |
| Example 1 | 0.81(6H, s) 0.95(6H, s) 1.85(12H, s) 2.20(12H, s) 2.42(12H, s) 6.20(4H, s) | C: 53.35 H: 6.42 | C: 52.96 H: 6.50 |
| Example 3 | 1.43(4H, t, J=7Hz) 1.57 (4H, t, J=7Hz) 1.79–1.87(8H, m) 1.83(12H, s) 2.20(12H, s) 2.39(12H, s) 6.21(4H, s) | C: 55.71 H: 6.55 | C: 55.87 H: 6.54 |
| Example 4 | 0.72(6H, s) 0.73(6H, s) 1.31(36H, s) 5.48(4H, t, J=2Hz) 5.97(4H, t, J=3Hz) 6.31(4H, t, J=2Hz) | C: 55.49 H: 6.94 | C: 55.75 H: 6.94 |
| Example 5 | 0.96(6H, s) 1.10(6H, s) 1.83(12H, s) 2.20(12H, s) 2.40(12H, s) 6.17(4H, s) | C: 48.10 H: 5.79 | C: 48.36 H: 5.77 |
| Example 6 | 0.97(6H, s) 1.10(6H, s) 1.90(12H, s) 2.23(12H, s) 2.48(12H, s) 6.13(4H, s) | C: 40.26 H: 4.88 | C: 40.76 H: 4.88 |
| Example 7 | −0.09(6H, s) 1.05(6H, s) 2.28(12H, s) 2.55(12H, s) 6.17(8H, s) 6.45(4H, s) 7.13(4H, s) | | |

What is claimed is:

1. A process for the preparation of metallocene complexes which comprises converting a part of an isomeric mixture of a metallocene complex represented by the formula (1):

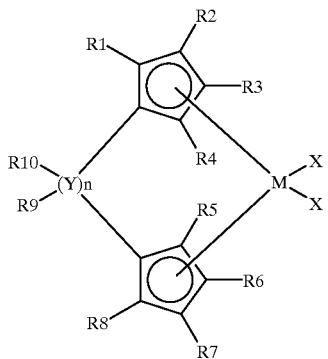

(1)

wherein M stands for a transition metal belonging Group III, IV, V, VI, Lantanoid or Actinoid of the Periodic Table, n stands for an integer of 1 or 2, Y stands for carbon, silicon, germanium or tin, X's may be the same or different and each independently stands for a halogen atom, a halogenoid atomic group, a hydrocarbon group having 1–20 carbon atoms which may contain a silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in the 5-membered or 6-membered ring or rings thereof and which may be substituted on the ring or rings thereof by other substituents, R1, R2, R3, R4, R5, R6, R7, R8, R9 and R10 may be the same or different and each stands for hydrogen, an alkyl group having 1–20 carbon atoms, a cycloalkyl group having 3–20 carbon atoms, an alkenyl group with 2–20 carbon atoms, an aryl group having 6–20 carbon atoms, an alkylaryl group having 7–20 carbon atoms, or an aralkyl group having 7–20 carbon atoms with the proviso that these groups may contain a silicon, germanium, oxygen, sulfur, or nitrogen, or a monocyclic or polycyclic heteroaromatic group which may contain a hetero atom or atoms selected from the group consisting of oxygen atoms, sulfur atoms and nitrogen atoms in the 5-membered or 6-membered ring or rings thereof and which may be substiututed on the ring or rings by other substituents with the proviso that the adjacent substituents on the cyclopentadienyl groups may form together a cyclic structure having 5–8 carbon atoms and the cyclic structure may be an aromatic ring, and that R9 and R10 may form together with Y a cyclic structure having 4–8 atoms and which may contain oxygen, sulfur and nitrogen, into a complex containing M—O bond, and then separating it.

2. A process for the preparation of metallocene complexes which comprises converting a part of an isomeric mixture of a metallocene complex represented by the formula (2):

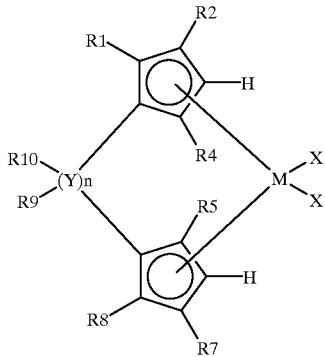

(2)

wherein M stands for titanium, zirconium or hafnium, n stands for an integer of 1 or 2, Y stands for carbon, silicon or germanium, X's may be the same or different and each independently stands for a halogen atom, a halogenoid atomic group, a hydrocarbon group having 1–20 carbon atoms which may contain a silicon, germanium, oxygen, sulfur, or nitrogen, R2 and R7 may be the same or different and each stands for an alkyl group having 1–20 carbon atoms, a cycloalkyl group having 3–20 carbon atoms, an alkenyl group having 2–20 carbon atoms, an aryl group having 6–20 carbon atoms, an alkylaryl group having 7–20 carbon atoms, or an aralkyl group having 7–20 carbon atoms which may include silicon, germanium, oxygen, sulfur and nitrogen, R1, R4, R5, and R8 may be the same or different and each stands for hydrogen, an alkyl group having 1–20 carbon atoms, a cycloalkyl group having 3–20 carbon atoms, an alkenyl group having 2–20 carbon atoms, an aryl group having 6–20 carbon atoms, an alkylaryl group having 7–20 carbon atoms, an aralkyl group having 7–20 carbon atoms which may include silicon, germanium, oxygen, sulfur, and nitrogen, or a monocyclic or polycyclic heteroaromatic group which may contain a hetero atom or atoms selected from the group consisting of oxygen atoms, sulfur atoms and nitrogen atoms in the 5-membered or 6-membered ring or rings thereof and which may be substituted on the ring or rings by other substituents with the. proviso that R1 and R2 as well as R7 and R8 may form together a cyclic structure having 5–8 carbon atoms which may be an aromatic ring, and that R7 and R8 may form together a cyclic structure having 4–8 carbon atoms which may include oxygen, sulfur and nitrogen, into a μ-oxo-complex represented by the formula (3).

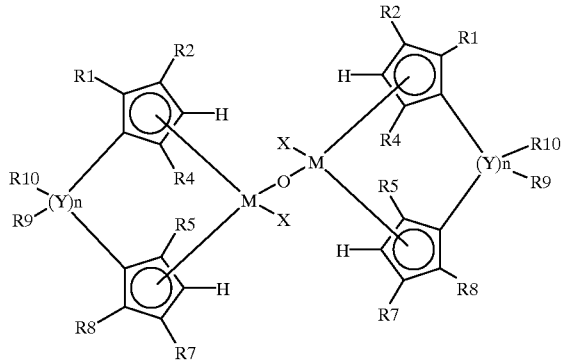

(3)

and then separating the $\mu$-oxo-complex.

3. A process for the preparation of metallocene complexes which comprises converting a part or the total amount of a meso form out of a mixture of the meso form and a racemic form of a metallocene complex represented by the aforesaid formula (2) into a $\mu$-oxo-complex represented by the aforesaid formula (3) and then separating the $\mu$-oxo-complex.

4. A process for the preparation of metallocene complexes which comprises reacting a mixture of a meso form and a racemic form of a metallocene complex represented by the aforesaid formula (2) wherein X stands for a halogen atom with water in the presence of a base thereby converting a part or the total amount of the meso form into a $\mu$-oxo-complex represented by the aforesaid formula (3) and then separating the $\mu$-oxo-complex.

5. The process of claim 2 wherein the isomeric mixture comprises a meso form and a racemic form of the metallocene complex represented by said formula (2) and wherein converting a part of the isomeric mixture comprises converting a part or the total amount of the meso form into a $\mu$-oxo-complex represented by said formula (3) and then separating the $\mu$-oxo-complex.

6. The process of claim 2 wherein the isomeric mixture comprises a meso form and a racemic form of the metallocene complex represented by said formula (2) and X stands for a halogen atom and wherein converting a part of the isometric mixture comprises reacting the mixture of the meso form and the racemic form with water in the presence of a base, thereby converting a part or the total amount of the meso form into a $\mu$-oxo-complex represented by said formula (3), and then separating the $\mu$-oxo-complex.

* * * * *